(12) United States Patent
Prencipe et al.

(10) Patent No.: US 10,130,597 B2
(45) Date of Patent: Nov. 20, 2018

(54) COMPOSITIONS AND DEVICES

(75) Inventors: Michael Prencipe, Princeton Junction, NJ (US); Richard Scott Robinson, Belle Mead, NJ (US); Rajnish Kohli, Hillsborough, NJ (US); Richard J. Sullivan, Atlantic Highlands, NJ (US); Diane Cummins, Livingston, NJ (US)

(73) Assignee: Colgate-Palmolive Company, New York, NY (US)

( * ) Notice: Subject to any disclaimer, the term of this patent is extended or adjusted under 35 U.S.C. 154(b) by 837 days.

(21) Appl. No.: 12/866,624

(22) PCT Filed: Feb. 6, 2009

(86) PCT No.: PCT/US2009/033303
§ 371 (c)(1),
(2), (4) Date: Aug. 6, 2010

(87) PCT Pub. No.: WO2009/100275
PCT Pub. Date: Aug. 13, 2009

(65) Prior Publication Data
US 2010/0322986 A1 Dec. 23, 2010

Related U.S. Application Data

(60) Provisional application No. 61/027,428, filed on Feb. 8, 2008.

(51) Int. Cl.
| | |
|---|---|
| *A61Q 11/00* | (2006.01) |
| *A61K 8/44* | (2006.01) |
| *A61K 8/64* | (2006.01) |
| *A61K 8/73* | (2006.01) |
| *A61K 8/85* | (2006.01) |
| *A61K 8/86* | (2006.01) |
| *A61K 8/88* | (2006.01) |
| *A61K 31/19* | (2006.01) |
| *A61K 8/02* | (2006.01) |
| *A61K 9/00* | (2006.01) |

(52) U.S. Cl.
CPC ............. *A61K 31/19* (2013.01); *A61K 8/02* (2013.01); *A61K 8/44* (2013.01); *A61K 9/0056* (2013.01); *A61Q 11/00* (2013.01)

(58) Field of Classification Search
CPC . A61Q 11/00; A61K 8/44; A61K 8/02; A61K 31/19
USPC ......................................................... 424/49
See application file for complete search history.

(56) References Cited

U.S. PATENT DOCUMENTS

| | | | |
|---|---|---|---|
| 3,535,421 A | 10/1970 | Briner et al. | |
| 3,678,154 A | 7/1972 | Widder et al. | |
| 3,925,543 A | 12/1975 | Donohue | |
| 3,932,605 A | 1/1976 | Vit | |
| 3,932,608 A | 1/1976 | Anderson et al. | |
| 3,943,241 A | 3/1976 | Anderson et al. | |
| 3,988,434 A | 10/1976 | Schole et al. | |
| 4,011,309 A | 3/1977 | Lutz | |
| 4,022,880 A | 5/1977 | Vinson et al. | |
| 4,025,616 A | 5/1977 | Haefele | |
| 4,042,680 A | 8/1977 | Muhler et al. | |
| 4,064,138 A | 12/1977 | Saari et al. | |
| 4,100,269 A | 7/1978 | Pader | |
| 4,108,979 A | 8/1978 | Muhler et al. | |
| 4,108,981 A | 8/1978 | Muhler et al. | |
| 4,146,607 A | 3/1979 | Ritchey | |
| 4,154,813 A | 5/1979 | Kleinberg | |
| 4,160,821 A | 7/1979 | Sipos | |
| 4,216,961 A | 7/1980 | Curtis et al. | |
| 4,225,579 A | 9/1980 | Kleinberg | |
| 4,259,316 A | 3/1981 | Nakashima et al. | |
| 4,269,822 A | 5/1981 | Pellico et al. | |
| 4,305,928 A | 12/1981 | Harvey | |
| 4,335,102 A | 6/1982 | Nakashima et al. | |
| 4,339,432 A | 7/1982 | Ritchey et al. | |
| RE31,181 E | 3/1983 | Kleinberg et al. | |
| 4,466,954 A | 8/1984 | Ichikawa et al. | |
| 4,528,181 A | 7/1985 | Morton et al. | |
| 4,532,124 A | 7/1985 | Pearce | |
| 4,538,990 A | 9/1985 | Pashley | |
| 4,645,662 A | 2/1987 | Nakashima et al. | |
| 4,656,031 A | 4/1987 | Lane et al. | |
| 4,725,576 A | 2/1988 | Pollock et al. | |
| 4,885,155 A | 12/1989 | Parran et al. | |
| 4,997,640 A | 3/1991 | Bird et al. | |
| 5,096,700 A | 3/1992 | Siebel et al. | |
| 5,141,290 A * | 8/1992 | Mairon ................. | A46B 11/00 15/167.1 |
| 5,286,480 A | 8/1994 | Boggs et al. | |
| 5,334,617 A | 12/1994 | Ulrich et al. | |
| 5,370,865 A | 12/1994 | Yamagishi et al. | |

(Continued)

FOREIGN PATENT DOCUMENTS

| | | |
|---|---|---|
| CA | 2526975 | 1/2005 |
| CA | 2566713 | 12/2005 |

(Continued)

OTHER PUBLICATIONS

Forward, G.C., Non-Fluoride Anticaries Agents, Advances in Dental Research, 1994, 8, pp. 208-214.*
Webster's Ninth New Collegiate Dictionary, Merriam-Webster Inc, Springfield, Massachusetts, USA, p. 405.*
Machado et al. CaviStat Confection Inhibition of Caries in Posterior Teeth, Abstract, 83rd Session of the American Association for Dental Research, Mar. 21-24, 2007, New Orleans, LA.
Chatterjee et al,. Bacterial Acidification and CaviStat Alkalinization of Occlusal Fissure pH, Abstract, 83rd Session of the American Association for Dental Research, Mar. 9-12, 2005, Baltimore, MD.
Kleinberg I., A Mixed-Bacteria Ecological Approach to Understanding the Role of the Oral Bacteria in Dental Caries Causation: An Alternative to *Streptococcus* Mutans and the Specific-Plaque Hypothesis, CRIT. Rev. Oral Biol. Med,. 12(2): 108-125 (2002).

(Continued)

*Primary Examiner* — Lezah Roberts

(57) ABSTRACT

The present invention provides oral instruments comprising a basic amino acid, to compositions for making such instruments, and to methods of making and using such instruments.

20 Claims, No Drawings

(56) References Cited

U.S. PATENT DOCUMENTS

| | | | |
|---|---|---|---|
| 5,693,795 | A | 6/1997 | Friedman et al. |
| 5,674,067 | A * | 10/1997 | Masel .................... A61C 7/303 433/18 |
| 5,747,004 | A | 5/1998 | Giani et al. |
| 5,762,911 | A | 6/1998 | Kleinberg et al. |
| 5,783,249 | A * | 7/1998 | Sanduja ............. A46B 11/0003 15/167.1 |
| 5,875,798 | A | 3/1999 | Petrus |
| 5,906,811 | A | 5/1999 | Hersh |
| 5,922,346 | A | 7/1999 | Hersh |
| 5,997,301 | A | 12/1999 | Linden |
| 6,217,851 | B1 | 4/2001 | Kleinberg et al. |
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,524,588 | B1 | 2/2003 | Kleinberg et al. |
| 6,805,883 | B2 | 10/2004 | Chevaus et al. |
| 8,075,216 | B2 | 12/2011 | Gatzemeyer et al. |
| 2002/0081360 | A1 | 6/2002 | Burgard et al. |
| 2002/0106345 | A1 | 8/2002 | Uhrich |
| 2003/0133885 | A1 | 7/2003 | Kleinberg et al. |
| 2003/0143315 | A1* | 7/2003 | Pui et al. ....................... 427/2.1 |
| 2003/0215513 | A1 | 11/2003 | Fyhr et al. |
| 2004/0038948 | A1 | 2/2004 | Uhrich |
| 2006/0140881 | A1 | 6/2006 | Xu et al. |
| 2006/0193791 | A1 | 8/2006 | Boyd et al. |
| 2007/0154863 | A1 | 7/2007 | Cai et al. |
| 2007/0181144 | A1* | 8/2007 | Brown et al. .................. 132/321 |
| 2008/0057103 | A1* | 3/2008 | Roorda .................... A61L 31/10 424/425 |

FOREIGN PATENT DOCUMENTS

| | | |
|---|---|---|
| CA | 2657323 | 1/2008 |
| CN | 1491608 | 4/2004 |
| EP | 0109359 | 5/1984 |
| EP | 413833 | 2/1991 |
| EP | 1736135 | 12/1996 |
| EP | 111604693 | 12/2005 |
| JP | 63-098357 A | 4/1988 |
| JP | H03-178926 | 8/1991 |
| JP | H07-100153 | 4/1995 |
| JP | H10-5250 | 1/1998 |
| JP | S63-220804 | 9/1998 |
| JP | H10-330507 | 12/1998 |
| JP | 2003-052723 | 2/2003 |
| JP | 2004-065707 | 3/2004 |
| JP | 2005-013375 | 1/2005 |
| JP | 2007-312828 A | 12/2007 |
| RU | 96112115 | 6/1996 |
| RU | 2238078 | 10/2004 |
| RU | 2269973 | 2/2006 |
| SU | 1808293 | 10/1990 |
| WO | WO199641617 | 10/1995 |
| WO | WO 97/032565 | 9/1997 |
| WO | WO00/33792 | 6/2000 |
| WO | WO 00/078270 | 12/2000 |
| WO | WO 2004/045446 | 6/2004 |
| WO | WO 2004/082628 | 9/2004 |
| WO | WO2005/000254 | 1/2005 |
| WO | WO2006/009737 | 1/2006 |
| WO | WO2006/060547 | 6/2006 |
| WO | WO2007008908 | 1/2007 |
| WO | WO2008/008617 | 1/2008 |

OTHER PUBLICATIONS

Kleinberg I., A New Salvia-Based Anticaries Composition, Dentistry Today, vol. 18, No. 2, Feb. 1999.

Acevedo et al., "The Inhibitory effect of an arginine bicarbonate/calcium carbonate (CaviStat)-containing dentifrice on the develpoment of dental caries in Venezuelean school children", The Journal of clinical Dentistry, 2005, v.16, No.3,pp. 63-70, ISSN 0895-8831.

DenClude Packaging with Ingredient List, 2004.

International Search Report and Written Opinion in International Application No. PCT/US09/033303, dated Sep. 24, 2009.

ProClude Packaging with Ingredient List, 2002.

* cited by examiner

COMPOSITIONS AND DEVICES

This application claims the benefit of U.S. Ser. No. 61/027,428 filed Feb. 8, 2008, the contents of which are incorporated herein by reference.

BACKGROUND OF THE INVENTION

Arginine and other basic amino acids have been proposed for use in oral care and are believed to have significant benefits in combating cavity formation and tooth sensitivity. It is believed that basic amino acids in the oral cavity are metabolized by certain types of bacteria, e.g., S. sanguis which are not cariogenic and which compete with cariogenic bacteria such as S. mutans, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities.

The treatment of the oral cavity with arginine is presently accomplished with dentifrice compositions, e.g., DenClude®. Food and drink products formulated with arginine are also proposed. Although the beneficial effect of arginine in the oral cavity may linger for minutes or hours following treatment, e.g., brushing teeth, chewing gum, or ingesting arginine enriched foods, it is desirable to develop other compositions and devices which deliver arginine to the oral cavity, e.g., in conjunction with arginine containing compositions, or alone.

Instruments for use in the oral cavity are well known in the art, and include, e.g., tooth brushes, tongue scrapers, dental floss, dental picks, mouth guards, and orthodontic corrective devices, e.g., braces and retainers. Although such instruments may be treated with a basic amino acid, the basic amino acid may leach or erode off the surface of such instruments, requiring repeated treatments which may be time consuming and inconvenient to the user. Treating such instruments is may also be complicated, as incomplete or incorrect treatment may result in too little, or too much basic amino acid being incorporated onto the surface of the instrument. Thus it is desirable to create compositions, devices and methods to overcome these problems.

SUMMARY OF THE INVENTION

The present invention is directed to compositions and devices which deliver basic amino acids, e.g., arginine, to the oral cavity to, e.g., reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5, (xi) reduce plaque accumulation, (xii) clean the teeth and oral cavity, (xiii) treat dry mouth, (xiv) improve systemic health, and/or (xv) whiten the teeth. Such compositions and devices may be used alone, or in conjunction with other basic amino acid containing compositions, e.g., dentifrice compositions to deliver a basic amino acid to the oral cavity.

The present invention thus includes Composition 1.0, a composition comprising a basic amino acid embedded in a bioerodable polymer.

The present invention also includes the following compositions:

1.1. Composition 1.0 wherein the basic amino acid is arginine, lysine, citrullene, ornithine, creatine, histidine, diaminobutanoic acid, diaminoproprionic acid, salts thereof and/or combinations thereof.

1.2. Composition 1.0 or 1.1 wherein the basic amino acid has the L-configuration.

1.3. Any of the preceding compositions wherein the basic amino acid is arginine.

1.4. Any of the preceding compositions wherein the basic amino acid is L-arginine.

1.5. Any of the preceding compositions comprising a basic amino acid in salt form.

1.6. Any of the preceding compositions comprising arginine phosphate.

1.7. Any of the preceding compositions comprising arginine hydrochloride.

1.8. Any of the preceding compositions comprising arginine sulfate.

1.9. Any of the preceding compositions comprising arginine bicarbonate.

1.10. Any of the preceding compositions wherein said bioerodable polymer is selected from poly(lactic acid), poly(glycolic acid) and copolymers; poly dioxanone, poly(ethyl glutamate), poly(hydroxybutyrate), polyhydroxyvalerate and copolymers, polycaprolactone, polyanhydride, poly(ortho esters), poly (iminocarbonates), polyester amides, polyester amines, polycyanoacrylates, polyphosphazenes, copolymers and other aliphatic polyesters, or suitable copolymers thereof including copolymers of poly-L-lactic acid and poly-e-caprolactone, fibrin, collagen, glycosoaminoglycans, oligosaccharides, poly saccharides, chondroitin, chitosan, alginate, fibring, fibrinogen, cellulosics, starches, dextran, dextrin, hyaluronic acid, heparin, elastin, multiblock copolymers, e.g., constructed from base units of glycolide, lactide, E-caprolactone, and polyethylene glycol, and poly(ester-amide) polymers or homologs, e.g., based on leucine, phenylalanine, and/or arginine, optionally with one or more diols and one or more dicarboxylic acids.

1.11. Any of compositions 1.0 et seq. further comprising a fluoride salt, e.g., selected from stannous fluoride, sodium fluoride, potassium fluoride, sodium monofluorophosphate, sodium fluorosilicate, ammonium fluorosilicate, amine fluoride, ammonium fluoride, and combinations thereof which resides in the pores.

1.12. Any of compositions 1.0 et seq. further comprising an antibacterial agent selected from triclosan, herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract, propolis), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.13. Any of the preceding compositions further comprising a whitening agent.

1.14. Any of the preceding compositions further comprising a whitening agent selected from a whitening active selected from the group consisting of peroxides, metal chlorites, perborates, percarbonates, peroxyacids, hypochlorites, and combinations thereof 1.15. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

In another embodiment, the present invention includes Composition 2.0, a composition comprising a porous scaffold and a basic amino acid residing within said pores.

The present invention also includes the following compositions:

2.1 Composition 2.0 wherein the basic amino acid is arginine, lysine, citrullene, ornithine, creatine, histidine, diaminobutanoic acid, diaminoproprionic acid, salts thereof and/or combinations thereof.

2.2 Composition 2.0 or 2.1 wherein the basic amino acid has the L-configuration.

2.3 Any of compositions 2.0-2.2 wherein the basic amino acid is arginine.

2.4 Any of compositions 2.0-2.3 wherein the basic amino acid is L-arginine.

2.5 Any of compositions 2.0-2.4 comprising a basic amino acid in salt form.

2.6 Any of compositions 2.0-2.5 comprising arginine phosphate.

2.7 Any of compositions 2.0-2.6 comprising arginine hydrochloride, 2.8 Any of compositions 2.0-2.7 comprising arginine sulfate.

2.9 Any of compositions 2.0-2.8 comprising arginine bicarbonate.

2.10 Any of compositions 2.0-2.9 wherein the basic amino acid reversibly resides within said pores.

2.11 Any of compositions 2.0-2.9 wherein the scaffold is a plastic selected from polyethylene, polymethyl methacrylate, polyurethane, polyethylene terephthalate, polypropylene, polystyrene, polyamides, bioplastic, and biodegradable plastics.

2.12 Any of compositions 2.0-2.10 wherein the scaffold is a bioerodable polymer.

2.13 Any of compositions 2.0-2.12 wherein the composition comprises from about 1% to about 50% by weight of the basic amino acid.

2.14 Any of compositions 1.0-2.13 further comprising a fluoride salt, e.g., selected from stannous fluoride, sodium fluoride, potassium fluoride, sodium monofluorophosphate, sodium fluorosilicate, ammonium fluorosilicate, amine fluoride, ammonium fluoride, and combinations thereof which resides in the pores.

2.15 Any of compositions 1.0-2.14 further comprising an antibacterial agent selected from triclosan, herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract, propolis), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

2.16 Any of the preceding compositions comprising a whitening agent.

2.17 Any of the preceding compositions comprising a whitening agent selected from a whitening active selected from the group consisting of peroxides, metal chlorites, perborates, percarbonates, peroxyacids, hypochlorites, and combinations thereof 2.18 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

2.19 Any of the preceding compositions effective upon application to the oral cavity, e.g., using an oral device, e.g. any of Devices 3.0.-3.8 to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) whiten teeth, (xvi) immunize the teeth against cariogenic bacteria; and/or (xvii) promote systemic health, including cardiovascular health, e.g., by reducing potential for systemic infection via the oral tissues.

2.20 A composition obtained or obtainable by combining the ingredients as set forth in any of the preceding compositions.

The invention further provides a device (Device 3.0) which is an oral instrument comprising a first material, said first material coated with any one of compositions 1.0-2.18, for example any of the following devices:

3.1 Device 3.0 wherein the instrument is a toothbrush comprising a head having bristles attached thereto.
3.2 Device 3.1 wherein one of compositions 1.0-2.19 coats said bristles.
3.3 Device 3.1 or 3.2 wherein one of compositions 1.0-2.19 coats said head.
3.4 Device 3.0 wherein the instrument is a toothpick.
3.5 Device 3.0 wherein the instrument is a tongue cleaner.
3.6 Device 3.5 wherein the tongue cleaner comprises a surface to clean the tongue, said surface being coated with one of compositions 1.0-2.19.
3.7 Devices 3.5 wherein the instrument is a mouth guard.
3.8 Devices 3.0 or 3.7 wherein the instrument is an orthodontic corrective device, e.g., a retainer.
3.9 Any of devices 3.0-3.7 when made by Method 4 or Method 5, as hereinafter set forth.

The present invention also encompasses Method 4, a method to manufacture a instrument for the oral cavity comprising:
1. dissolving a bioerodable polymer or monomer thereof in a solvent to form a solution;
2. admixing a basic amino acid in said solution;
3. removing said instrument from said solution to coat said instrument with said solution; and
4. evaporating the solvent.

Preferably, the instrument is insoluble, or substantially insoluble in the solvent.

The present invention also encompasses Method 5, a method to manufacture a instrument for the oral cavity comprising:
1. admixing a basic amino acid with a monomer, said monomer which can polymerize to form a bioerodable polymer;
2. immersing an instrument in the mixture
3. removing said instrument from the mixture; and
4. and treating the cleaning instrument under conditions to induce polymerization of the monomer to form a bioerodable polymer.

The invention further provides a method (Method 6) comprising a method to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) whiten teeth, (xvi) immunize the teeth against cariogenic bacteria; and/or (xvii) promote systemic health, including cardiovascular health, e.g., by reducing potential for systemic infection via the oral tissues comprising use of an oral device comprising, a basic amino acid, e.g. any of Devices 3.0.-3.9, by a person in need thereof.

The invention further comprises the use of a basic amino acid in the manufacture of a dental device, e.g., any of Devices 3.0-3.9, as hereinbefore described, e.g., for use in a method of manufacture as hereinbefore described, e.g., Method 4 or 5, or a method of use as hereinbefore described, e.g., Method 6.

Other embodiments of the present invention will be apparent to one of skill in the art.

DETAILED DESCRIPTION OF THE INVENTION

As used herein, a bioerodable polymer is a polymer which may be degraded by exposure to the oral cavity. Degradation may he caused when the material comes into contact with substances in the oral cavity, e.g., saliva. Degradation may also be caused due to friction and irritation between the polymer and the oral cavity. Depending on the thickness of the polymer, only the surface of the polymer coming into contact with the oral cavity is degraded.

An "effective amount" is an amount that is sufficient to have a desired therapeutic or prophylatic effect in the oral cavity without undue adverse side effects such as irritation or allergic response.

Unless otherwise indicated, as used herein, a basic amino acid includes a basic amino acid as free base and/or salts thereof.

Instruments for use in the oral cavity are well known in the art, and include, e.g., tooth brushes, tongue scrapers, dental floss, dental picks, mouth guards, and orthodontic corrective devices, e.g., braces and retainers. Instruments for use in the oral cavity are not limited to cleaning and orthodontic corrective devices. Other instruments include objects designed to be used in the oral cavity, such as pacifiers (also known as a comforter, or soother), and chew toys for toddlers and infants, such as teething rings. Other instruments include objects which are not designed for use in the mouth, but humans may put such objects into their mouths, such as pens and pencils.

Although such instruments may be treated with a basic amino acid, e.g., surface coated, it is desirable to incorporate basic amino acids directly in to the instrument so as to avoid the need to repeat such treatment. This may be accomplished by coating the instrument with a bioerodable polymer comprising a basic amino acid, or manufacturing the instrument with the same. As the surface of the polymer is exposed in the oral cavity, the basic amino acid on the surface of the polymer is released into the oral cavity. As the surface of the polymer is eroded, e.g., during normal use in the oral cavity, additional basic amino acid becomes available for release into the oral cavity.

Incorporating basic amino acids directly into the instrument may also be accomplished by use of a porous material. The instrument may be manufactured from the porous material, or coated with the same. Generally, the material contains pores which the basic amino acid resides in. The amino acid is released when the instrument is used, e.g., in the oral cavity. If the pores release the amino acid contained there, the porous material may be treated by exposure to the basic amino acid to refill the pores. Thus, the basic amino acid may be released from, or captured in the pores.

Methods for manufacturing instruments for use in the oral cavity are also well known in the art, as well as compositions for making the same. The present invention also contemplates manufacturing such instruments with it composition comprising a bioerodable polymer and a basic amino acid, or a porous scaffold having a basic amino acid.

Bioerodable polymers are well known to those of skill in the art, and include poly(lactic acid), poly(glycolic acid) and copolymers, poly dioxanone, poly(ethyl glutamate), poly (hydroxybutyrate), polyhydroxyvalerate and copolymers, polycaprolactone, polyanhydride, poly(ortho esters), poly (iminocarbonates), polyester amides, polyester amines, polycyanoacrylates, polyphosphazenes, copolymers and other aliphatic polyesters, or suitable copolymers thereof including copolymers of poly-L-lactic acid and poly-e-caprolactone; mixtures, copolymers, and combinations thereof. Other useful polymers may also include polyacrylates, polymethacryates, polyureas, polyurethanes, polylefins, polyvinylhalides, polyvinylidenehalides, polyvinylethers, polyvinalaromatics, polyvinylesters, polyactylonitriles, resins, polysiloxanes, epoxy resins, and polytetrafluoroethylene. Other useful polymers may include or be based on fibrin, collagen, glycosoaminoglycans, oligosaccharide and poly saccharides, chondroitin, phosholipids, phosphorylcholine, chitosan, alginate, fibring, fibrinogen, cellulosics, starches, dextran, dextrin, hyaluronic acid, heparin, and elastin. The polymer may also be a multiblock copolymers, e.g., constructed from base units of glycolide, lactide, E-caprolactone, and polyethylene glycol. Useful polymers also include poly(ester-amide) polymers or homologs based on leucine, pheylalanine, and/or arginine, optionally with one or more diols and one or more dicarboxylic acids.

Methods for forming such polymers, e.g., from monomers, are well known in the art. Methods for inducing polymerization are known in the art, e.g., dissolving in a solvent, exposure to radiation, including visible and UV radiation, and heat treatment.

Porous scaffolds are known in the art, and include plastic, ceramic, and other materials. Plastics and their formation are well known in the art, and include polyethylene, polymethyl methacrylate, polyurethane, polyethylene terephthalate, polypropylene, polystyrene, polyamides, bioplastic, and biodegradable plastics. The size of the pores is important in that small pore sizes are unable to absorb and release the basic amino acid, and large pores will require constant loading. In one embodiment of the present invention, the pores are on average from about 10 μm to about 500 μm in diameter, e.g., about 10 μm, 20 μm, 30 μm, 40 μm, 50 μm, 60 μm, 70 μm, 80 μm, 90 μm, 100 μm, 200 μm, 300 μm, or 400 μm in diameter.

The basic amino which can be used in the compositions of the present the invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, l-arginine.

The basic amino acid may be added to the bioerodable polymer, prior to or during polymerization as a free base or salt form. As used herein, reference to a basic amino acid also includes salts thereof. As the compositions and devices of the invention are intended for use in the mouth, salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

The compositions of the present invention comprise an effective amount of a basic amino acid. Thus, the composition may comprise from about 1% to about 50% by weight of a basic amino acid, e.g., about 1, 2, 3, 4, 5, 10, 15, 20, 25, 30, 35, 40 or 45%.

In one embodiment, the basic amino acid is soluble in the polymer. In a preferred embodiment, the basic amino acid is insoluble in the polymer. If the amino acid is insoluble, it is preferred that the amino acid particle size is sufficiently small so as to not cause irritation to the oral cavity when used in the oral cavity. Preferably, the amino acid is evenly distributed in the polymer.

In one embodiment the polymer is an anionic polymer, for example a polycarboxylate polymer, e.g., an acrylate polymer or copolymer, wherein the basic amino acid forms a salt with the carboxylate moieties in the polymer.

In one embodiment of the present invention, the bioerodable polymer or porous scaffold may optionally include an effective amount of fluoride, or a fluoride ion source. A wide variety of fluoride ion-yielding materials can be employed as sources of soluble fluoride in the present compositions. Examples of suitable fluoride ion-yielding materials are found in U.S. Pat, No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In another embodiment of the present invention, the bioerodable polymer or porous scaffold may optionally comprise an antiseptic or antimicrobial selected from triclosan, herbal extracts and essential oils (e.g., rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis, and combinations thereof to further aid in the beneficial effects of the basic amino acid.

When coated on an instrument, the biopolymer or porous scaffold is preferably thin enough so as to not impair use of the instrument, but thick enough so that a sufficient amount of polymer remains coated on to the instrument for subsequent normal use, e.g., used 3, 4, 5, 10, 15, 20, 25, 30, 60, or 90 times. Normal use of the instrument will depend on the particular instrument. The biopolymer may be from about 0.1 μm to about 3000 μm thick, about 1 μm, 5 μm, 10 μm, 25 μm, 50 μm, 100 μm, 250 μm, 500 μm, 1000 μm, 2000 μm, or about 3000 μm thick. The thickness of the coating will depend on the particular instrument.

The compositions of the present invention may also include flavors. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The compositions of the present invention may also include colors. Use of flavors and colors may aid in determining if the scaffold contains the amino acid, or the degree of degradation of the bioerodable polymer.

The compositions of the present invention may also be used as adhesives in the oral cavity, e.g., adhesive for brackets used with orthodontic braces. The compositions of the present invention may also be used as adhesives in the production of instruments, e.g., to adhere a toothbrush head to the handle. The present invention may also be used as a dental sealant, e.g., a protective coating.

EXAMPLE 1

A clear mouth guard suitable for use in contact sports is coated with a bioerodable polymer comprising 40% by weight L-arginine and flavoring, e.g., mint. The surface of the polymer is degraded during use, releasing L-arginine into the oral cavity, e.g., to reduce or inhibit formation of dental caries, reduce, repair or inhibit pre-carious lesions of the enamel, reduce or inhibit demineralization and promote remineralization of the teeth, reduce or inhibit gingivitis, reduce levels of acid producing bacteria, increases the relative levels of arginolytic bacteria, and raise and/or maintain plaque pH at levels of at least pH 5.5. Repeated use of the mouth guard further degrades the polymer, and the user knows the polymer is completely degraded when the mouth guard no longer has a mint taste.

EXAMPLE 2

A pacifier is manufactured with a porous plastic scaffold having an average pore diameter of 50 um. The pacifier is soaked in a cleaning solution comprising arginine bicarbonate, and the arginine bicarbonate is absorbed into the pores.

EXAMPLE 3

The pacifier of Example 2 is given to an infant for normal use, i.e., sucking, and chewing. As the infant sucks and chews on the pacifier, arginine bicarbonate is released into the oral cavity, e.g., to inhibit microbial biofilm formation in the oral cavity.

EXAMPLE 4

The used pacifier of Example 3 is soaked in the cleaning solution comprising arginine bicarbonate.

EXAMPLE 5

A clear toothbrush head is coated with a bioerodable polymer comprising arginine and a color, e.g., red. Bristles are attached to the head, and the head is attached to a handle. Use of the toothbrush in the oral cavity releases arginine as the polymer is degraded. The user knows that the head or toothbrush requires replacement when the head is no longer red.

The invention claimed is:

1. An instrument, wherein at least a portion of the instrument is coated with a composition comprising a scaffold having pores, and a basic amino acid residing within said pores, wherein said pores are on average from about 10 µm to about 500 µm in diameter, and wherein the instrument is a toothbrush comprising a head having bristles attached thereto.

2. The instrument of claim 1 wherein the basic amino acid is selected from arginine, lysine, citrullene, ornithine, creatine, histidine, diaminobutanoic acid, diaminopropionic acid, salts thereof and combinations thereof.

3. The instrument of claim 1 wherein the basic amino acid has the L-configuration.

4. The instrument of claim 1 wherein the basic amino acid is arginine.

5. The instrument of claim 3 wherein the basic amino acid is L-arginine.

6. The instrument of claim 1 wherein said basic amino acid is in salt form.

7. The instrument of claim 6, wherein the salt form of said basic amino acid is arginine phosphate.

8. The instrument of claim 6, wherein the salt form of said basic amino acid is arginine hydrochloride.

9. The instrument of claim 1, wherein the composition further comprises an anionic polymer.

10. The instrument of claim 6, wherein the salt from of said basic amino acid is arginine bicarbonate.

11. The instrument of claim 1 wherein the bristles are coated.

12. The instrument of claim 1 wherein the head is coated.

13. A method to: (1) reduce or inhibit formation of dental caries, (ii) reduce repair or inhibit pre-caries lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) increase relative levels of arginonlytic bacteria, (ix) inhibit microbial biofilm formation in the oral cavity, (x) raise and/or maintain plaque pH levels of at least pH 5.5 following sugar challenge, (xi) reduce plaque accumulation, (xii) treat, relieve or reduce dry mouth, (xiii) clean the teeth and oral cavity, (xiv) reduce erosion, (xv) whiten teeth, (xvi) immunize the teeth against cariogenic bacteria; and or (xvii) promote systemic health, including cardiovascular health, e.g. by reducing potential for systemic infection via the oral tissues; comprising use of an instrument according to claim 1 by a person in need thereof.

14. The instrument of claim 1, the composition further comprising a fluoride ion source.

15. The instrument of claim 14, wherein said fluoride ion source is selected from stannous fluoride, sodium fluoride, potassium fluoride, sodium monofluorophosphate, sodium fluorosilicate, ammonium fluorosilicate, amine fluoride, ammonium fluoride, and combinations thereof.

16. The instrument of claim 1, the composition further comprising a potassium ion source.

17. The instrument of claim 16, wherein said potassium ion source is selected from potassium nitrate and potassium chloride.

18. The instrument of claim 1 wherein the scaffold comprises a plastic.

19. The instrument of claim 1 wherein the scaffold comprises a material selected from polyethylene, polymethyl methacrylate, polyurethane, polyethylene terephthalate, polypropylene, polystyrene, polyamides, bioplastic, biodegradable plastics, and combinations thereof.

20. The instrument of claim 1 wherein the basic amino acid reversibly resides within said pores.

* * * * *